US00PP27936P2

(12) United States Plant Patent
Hansen

(10) Patent No.: US PP27,936 P2
(45) Date of Patent: Apr. 25, 2017

(54) ***HIBISCUS* PLANT NAMED 'BERRY AWESOME'**

(50) Latin Name: ***Hibiscus* hybrid (L.)**
Varietal Denomination: Berry Awesome

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 7 days.

(21) Appl. No.: 14/757,105

(22) Filed: Nov. 19, 2015

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy herbaceous perennial *Hibiscus* hybrid plant named 'Berry Awesome' comprising a short compact habit of multiple, well-branched, basal stems producing numerous flowers over a prolonged season having lavender-pink, overlapping petals and a cherry-red lustrous eye. The petals have radial pleating along veins which helps resist strong wind, bright sun and harsh rain conditions. The foliage is dark-green, primarily heavily-dissected and tri-lobed. Foliage is dark-green, purple-tinged with deeply dissected maple-like shape.

1 Drawing Sheet

Botanical classification: *Hibiscus* hybrid (L.).
Variety denomination: 'Berry Awesome'.

BACKGROUND AND ORIGIN OF THE PLANT

The present invention relates to the new and distinct hardy, herbaceous, *hibiscus* plant, *Hibiscus* 'Berry Awesome' hybridized by the inventor on Aug. 3, 2011 at a nursery in Zeeland, Mich. The new plant is from a cross between *Hibiscus* 'Crown Jewels' U.S. Plant Pat. No. 11,857 (female seed parent) times 'Cranberry Crush' U.S. Plant Pat. No. 21,984 (male pollen parent). Both parents have a complex mixture of species in them, most likely including the species: *moscheutos, coccineus* and *laevis* (formerly *H. militaris*). Seed from the above cross was harvested on Nov. 7, 2011 and the single seedling was later identified with the breeder code 11-107-101 after selection in 2013. *Hibiscus* 'Berry Awesome' was first asexually propagated in 2013 by sterile shoot-tip tissue culture at the same nursery in Zeeland, Mich. The resultant asexually propagated plants from both methods have been found to be stable and true to type in successive generations of asexual reproduction.

No plants have been sold, either in this country or anywhere in the world, prior to the filing of this application, nor has any disclosure been made prior to the filing of this application with the exception of that which was within one year of the filing of this application and was derived directly or indirectly from the inventor.

BRIEF SUMMARY OF THE PLANT

*Hibiscus* 'Berry Awesome' differs from its parents as well as all other hardy herbaceous *hibiscus* known to the applicant in many traits. The most similar *hibiscus* in flower color known to the applicant is 'Berrylicious' U.S. Plant Pat. No. 24,062, habit of the new plant is more compact, the foliage is darker greyed-purple tinged. Other similar *hibiscus* including: 'Fantasia' U.S. Plant Pat. No. 11,853 and 'Plum Crazy' U.S. Plant Pat. No. 11,854. 'Fantasia' and 'Plum Crazy' are slower growing, produce fewer stems, branches per stem and flowers per stem. The flowers of 'Plum Crazy' are more reddish than the new plant. Compared to the parents, the flowers of 'Berry Awesome' are more purple and less red. The flower of 'Crown Jewels' is smaller than the new plant, and the color is near white with a red eye.

*Hibiscus* 'Berry Awesome' is a unique hardy herbaceous *hibiscus* with the following combined traits:

1. Winter-hardy, perennial with short compact habit of multiple, well-branched, basal stems.
2. Many flowers over a prolonged season having lavender-pink overlapping petals and a lustrous eye of cherry-red.
3. Petals have radial pleating or folding giving the appearance of a three-dimensional petals and helping resist strong wind, bright sun and rain conditions.
4. Dark-green, purple-tinged, deeply-dissected, maple-like foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
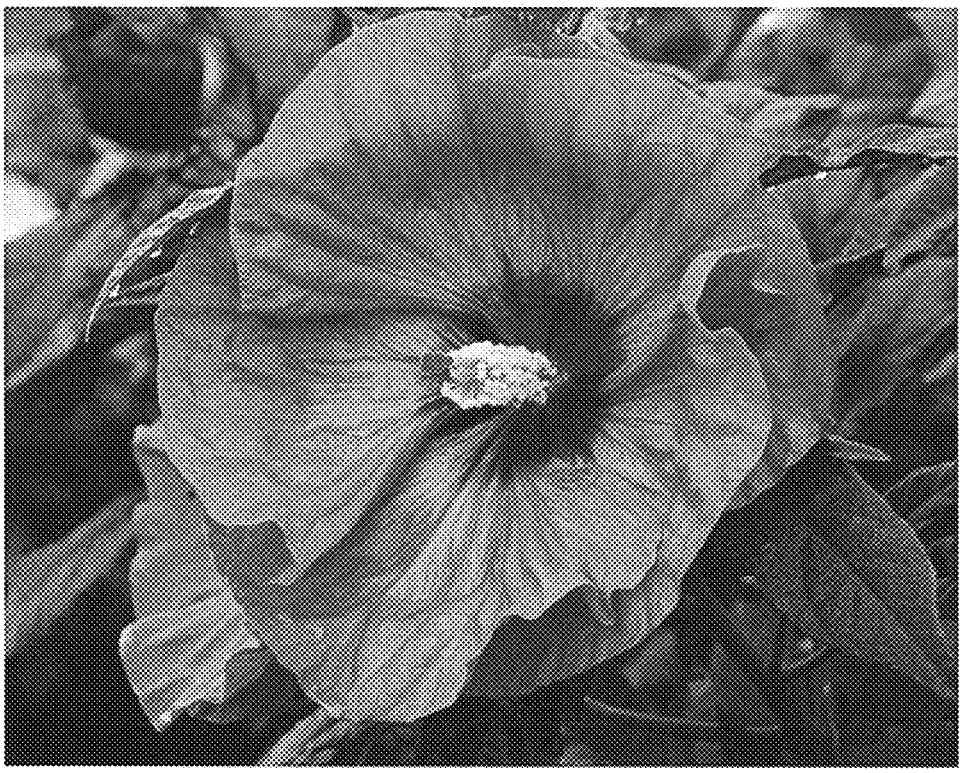
FIG. 1 shows a close-up of the flowers with radially pleated or folded lavender pink petals.
Figure 2:
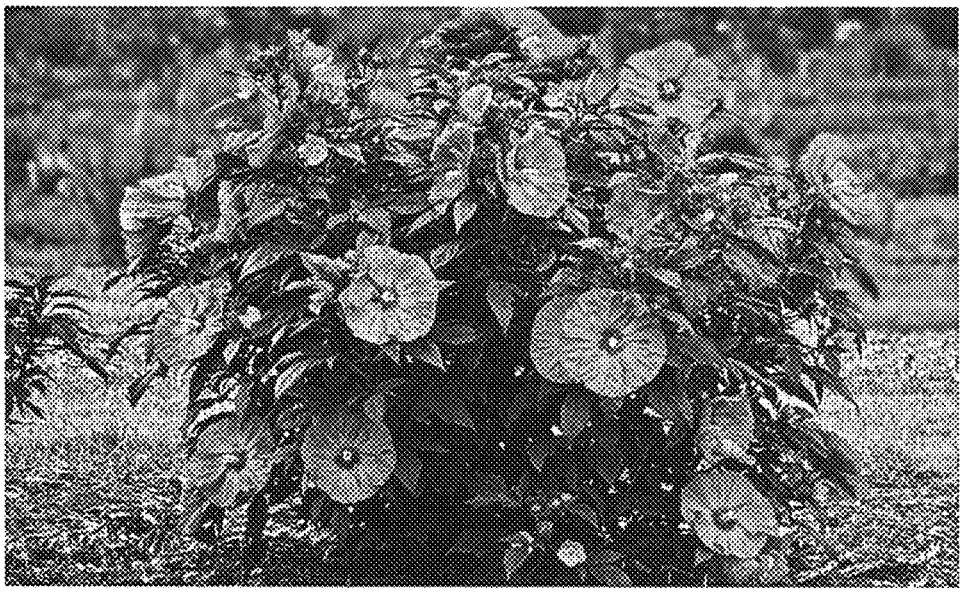
FIG. 2 shows a three-year old plant in the landscape.

The following descriptions and color references are based on the 2001 edition of The Royal Horticultural Society Colour Chart except where common dictionary terms are used. The new plant, *Hibiscus* 'Berry Awesome', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: *Hibiscus* 'Crown Jewels' U.S. Plant Pat. No. 11,857 (female seed parent) times *Hibiscus* 'Cranberry Crush' U.S. Plant Pat. No. 21,984 (male pollen parent).

Propagation:

*Method*.—Stem cuttings and sterile shoot-tip plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with 40 to 48 thick upright and heavily branched main stems producing a upright spreading mound to about 137.0 cm tall and 180.0 cm wide, widest about 100 cm above soil line; 7 to 9 primary branches per main stem protruding at 60° to 45° angle from vertical, lateral branches on the proximal one third to one half of the primary branches; secondary branches rare; flowering from base to top of plant with about 48 to 54 flowers per main stem.

*Stem*.—Terete, glabrous, glaucous; to about 137.0 cm tall and about 1.6 cm diameter at base, average about 120.0 cm tall and about 12.0 mm diameter at base.

*Stem color*.—Base between RHS 138B and RHS 147C with tinting in high light exposed portions of nearest RHS 182B; distal portion between RHS 183A and RHS 187B.

*Lateral branches*.—Terete, glabrous, glaucous; to about 38.5 cm long and 6.0 mm diameter.

*Lateral branch color*.—Between RHS 178A and RHS 183C.

*Internode*.—About 12 nodes per stem below flowers, average internode length about 5.0 cm of unpinched plant, widest in middle portion of stem.

*Internode color*.—Varying with light exposure, same as surrounding stem.

Foliage description: Alternate; dentate; glabrous; deeply cleft, mostly three or five-lobed; sparsely and finely puberulent above and below; with side lobes at about 80 degree angle from center lobe; texture above and below matte; leave blades to about 17.0 cm long and about 18.0 cm across, leaf blade size average 15.5 cm long and 14.0 cm wide, becoming smaller in distal portion of stem; no fragrance detected.

*Foliage color*.—Adaxial side between RHS N187A and RHS 187A with a green base of nearest RHS 141B; abaxial nearest RHS 147B.

*Veins*.—Palmate; sparsely and finely puberulent.

*Vein color*.—Adaxial primary and secondary veins nearest RHS N186C; abaxial nearest RHS 161A in main leaf body with dominant pigment of nearest RHS 183B toward margins with densely speckling of nearest RHS 183D toward leaf base.

*Petioles*.—Mostly terete, finely puberulent; to about 9.5 cm long and 7.0 mm diameter at base, average size about 8.0 cm long and 6.0 mm wide.

*Petiole color*.—Adaxial between RHS 187B and RHS 187C; abaxial nearest RHS 183C.

Flower description: Complete; actinomophic; rotate; upward to outward facing; lasting about two days on plant; no fragrance detected.

*Buds one day prior to opening*.—Ovoid with acute apex and bluntly rounded base; carinate at sepal fusions; unopened petals wrinkled at veins; about 5.2 cm long and about 5.0 cm across.

*Bud color*.—Exposed petal color nearest RHS 59B; color of sepals between RHS 141C and RHS 143C without distinctly colored veining.

*Epicalyx*.—Entire, abaxial and adaxial finely puberulent, linear with sharply acute apex and attenuate base, curved around sepals; matte surfaces; typically 10 to 12 per flower; about 2.5 cm long tapering to base of about 3.0 mm wide; adaxial and abaxial color between RHS 141C and RHS 143C.

*Sepals*.—Five, acute apex; margin entire, edentate; abaxial and adaxial surfaces matte; fused in base; about 3.1 cm long, fused in about the basal 1.3 cm, about 2.0 cm wide at fusion, proximal 1.8 cm connate forming campanulate star-shaped calyx.

*Sepal color*.—Abaxial nearest RHS 144A, adaxial color nearest RHS 144B.

*Flowers*.—Solitary, 48 to 54 per main stem without pinching; slightly cupped petals and lightly pleated at veins; upward and outwardly facing; average 20.0 cm across and 5.5 cm deep from outside face to inside base of petals, larger in early part of flowering season; persist for a one to two days; effective for at least 10 weeks beginning late-July and lasting into October; no detectable fragrance.

*Petals*.—Five; glabrous, slightly lustrous in center and dull both front and back toward middle and perimeter; adnate to the androecium to form a column, imbricate to about 75% overlapping at widest part (petals overlapping all but 25% of the petals to either side), palmately veined, primary and secondary veins impressed on front and ribbed on back; shape: rounded with distinct claw and limb; margins: entire, edentate; apex: rounded; base: short claw-like; size: average about 10.5 cm long and about 14.0 cm wide at widest portion (larger in earlier part of flowering season); center dark eye about 6.5 cm diameter.

*Petal color*.—Adaxial as first opening nearest RHS 60C and between RHS 70C and RHS 70B when fully opened with a darker eye of between RHS 53A and RHS 60A; abaxial color between RHS 70B and RHS 70C with exposed eye between RHS 61C and RHS 61B; adaxial vein color nearest RHS 61B for about 5.0 cm then blending with distal portion of petal, adaxial veins nearest RHS 61B.

*Gynoecium*.—Single; partially enclosed in column. Column: glabrous, lustrous; about 5.7 cm long and 1.5 cm wide at base. Column color: basal 1.0 cm nearest RHS 61B, then next proximal 1.0 cm nearest 62D with distal 4.2 cm with longitudinal ridges of RHS 61B and RHS 62C. Style: protruding from column and split in distal about 7.0 mm portion into typically five branches and protrudes from column, branch diameter about 1.5 mm; branch color nearest RHS 59C. Stigma: typically five; globose, puberulent, about 2.5 mm in diameter; color nearest RHS 59C. Ovary: superior, about 9.0 mm across at base and about 10.0 mm tall; acute apex; color between RHS 145B and RHS 145C.

*Androecium*.—Filaments: numerous, about 150; less than about 1.0 mm in diameter and about 6.0 mm long; attached along nearly the entire length of column; color variable, some nearest RHS 59C others nearest RHS N155C. Anthers: reniform; dorsifixed; about 2 mm long and 1 mm wide; color between RHS 151A and RHS 11C. Pollen: numerous, globose, less than 0.1 mm long; color nearest RHS 12C.

*Pedicel*.—Terete, finely puberulent; length from base of sepal to abscission point average 1.2 cm long and 4.0 mm wide, longer on early flowers decreasing in distal flowers; color nearest RHS 138B.

*Peduncle*.—Terete, finely puberulent flowers are held easily visible on average 7.0 cm long from abscission point to stem and 4.0 mm wide, longer on earlier and lower flowers; color nearest RHS 138B distally just below abscission point, becoming nearest RHS 182B in higher direct sun exposure.

*Fruit*.—Loculicidal capsule; puberulent; globose, with abruptly acute apex; color between RHS N199B and RHS N199C when mature.

*Seed*.—Minutely floccose, typically globose; about 3.0 mm in diameter; color between RHS 200A and RHS N199B.

Resistance: The flowers of 'Berry Awesome' have resisted wind, rain and hot sun conditions better than typical hardy perennial *hibiscus*. Other pest and disease resistance beyond that of other hardy perennial *hibiscus* cultivars has not been observed. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Berry Awesome' as herein illustrated and described, suitable for potted plant culture, landscaping as a specimen or en masse, and especially suited for patios and confined spaces because of the short compact habit.

* * * * *